(12) United States Patent
Montgomery

(10) Patent No.: US 6,719,707 B1
(45) Date of Patent: Apr. 13, 2004

(54) APPARATUS AND METHOD FOR PERFORMING MUSICAL PERCEPTION SOUND ANALYSIS ON A SYSTEM

(76) Inventor: Nathan Montgomery, 515 S. Edgeworth, Royal Oak, MI (US) 48067

( * ) Notice: Subject to any disclaimer, the term of this patent is extended or adjusted under 35 U.S.C. 154(b) by 0 days.

(21) Appl. No.: 09/939,281

(22) Filed: Aug. 24, 2001

Related U.S. Application Data
(60) Provisional application No. 60/298,445, filed on Jun. 15, 2001.

(51) Int. Cl.[7] ................................................ A61B 7/00
(52) U.S. Cl. ..................................................... 600/586
(58) Field of Search ........................ 600/586; 84/477 R, 84/600, 603, 609, 723, 454; 704/268; 434/185, 307 R; 709/203

(56) References Cited

U.S. PATENT DOCUMENTS

| | | |
|---|---|---|
| 3,855,416 A | 12/1974 | Fuller |
| 3,855,418 A | 12/1974 | Fuller |
| 3,971,034 A | 7/1976 | Bell, Jr. et al. |
| 5,148,483 A | 9/1992 | Silverman |
| 5,524,173 A * | 6/1996 | Puckette ..................... 704/268 |
| 5,563,358 A * | 10/1996 | Zimmerman .............. 84/477 R |
| 5,774,850 A | 6/1998 | Hattori et al. |
| 5,964,593 A | 10/1999 | Cohen |
| 6,006,188 A | 12/1999 | Bogdashevsky et al. |
| 6,046,724 A | 4/2000 | Hvass |
| 6,056,703 A | 5/2000 | Sandler et al. |
| 6,151,571 A | 11/2000 | Pertrushin |
| 6,157,913 A | 12/2000 | Bernstein |
| 6,173,260 B1 | 1/2001 | Slaney |
| 6,296,489 B1 * | 10/2001 | Blass et al. .................. 434/185 |
| 6,417,435 B2 * | 7/2002 | Chantzis et al. .......... 84/477 R |

OTHER PUBLICATIONS

Zeskind PS, Marshall TR, Goff DM "Cry Threshold Predicts Regulatory Disorders In Newborn Infants." 1996.
Hadjistavropoulos HD, Craig KD, Grunau RV, Johnson CC "Judging Pain In Newborns: Facial and Cry Determinants." 1994.
Robb MP, Cacace AT; "Estimation of Format Frequencies in Infant Cry", 1995.
Cacace AT, Robb MP, Saxman JH, Risemberg H, Koltai P; Acoustic Features Of Normal–Hearing Pre–Term Infant Cry; 1995.
Raes J, Michelsson K, Dehaen F., Despontin M; "Cry Analysis In Infants With Infectious And Congenital Disorders Of The Larynx" 1982.
St. James–Roberts I, Hurry J, Bowyer J; "Ojective Confirmation of Crying Durations In Infants Referred For Excessive Crying." 1993.
Robb MP, Cacace AT; "Estimation Of Formant Frequencies In Infant Cry" 1995.

(List continued on next page.)

*Primary Examiner*—Max F. Hindenburg
*Assistant Examiner*—Brian Szmal
(74) *Attorney, Agent, or Firm*—Howard & Howard

(57) ABSTRACT

An apparatus and method analyze a system using musical perception sound analysis. A transducer receives acoustic events generated by the system. An analysis module is coupled to the transducer and receives the acoustic events, monitors the system as a function of a set of musical perception parameters and responsively identifies a presence of a predetermined condition.

111 Claims, 7 Drawing Sheets

OTHER PUBLICATIONS

Johnston CC, Stevens B, Craig KD, Grunau RV; "Development Changes In Pain Expression In Premature, Full–Term, Two–And Four–Month–Old Infants" 1993.

Grunau RV, Johnston CC, Craig KD; "Neonatal Facial And Cry Responses To Invasive And Non–Invasive Procedures." 1990.

Huffman, et al; "Infant Cry Acoustics And Maternal Ratings Of Trmperament" 1994.

Zeskind, Klein, Marshall; "Adults' Perceptions Of Experimental Modifications Of Durations Of Pauses and Expiratory Sounds In Infant Crying" 1992.

Legerstee, Bowman, Fels; "People And Objects Affect The Quality Of Vocalizations In Infants With Doen Syndrome" 1992.

Lester, Boukydis, Garcia–Coll, Hole, et al.; "Infantile Colic: Acoustic Cry Characteristics, Maternal Perception Of Cry, And Temperament" 1992.

Gerber SE; "Acoustical Analyses Of Neonates' Vocalizations" 1985.

Stolyarova, E.I.; The Possibility Of Differential Assessment Of Pain–Induced Vocalization During Auditory Analysis; 1999.

Lester, Barry M., Ph.D.; "Developmental Outcome Prediction From Acoustic Cry Analysis In Term And Preterm Infants" 1987.

Donzelli, Rapisardi, Moroni, et al. "Computeried Cry Analysis In Infants Affected By Sever Protein Energy Malnutrition" 1994.

Gort, Manfredi; "Acoustic Analysis Of Newborn Infant Cry Signals" 1998.

Runefors, Arnbjornsson, Elander and Michelsson; "Newborn Infants Cry After Heel–Prick: Analysis With Sound Spectrogram" 2000.

Green, Gustafson, Mc'Ghi; Changes In Infants' Cries As A Function Of Time In A Cry Bout 1998.

Zeskin, Barr; Acoustic Characteristics; "Acoustic Characteristics Of Naturally Occuring Cries Of Infants With 'Colic'"; 1997.

Moller, Schonweiler; "Analysis Of Infant Cries For The Early Detection Of Hearing Impairment"; 1999.

Michelsson, Christensson, Rothganger and Winberg; "Crying In Separated And Non–Separated Newborns: Sound Spectrographic Analysis" 1996.

Stolyarova, E.I.; "The Possibility Of Differential Assessment Of Pain Induced Vocalization During Auditory Analysis" 1999.

Brennan, Kirkland; "Perceptual Dimensions Of Infant Cry Signals: A Semantic Differential Analysis" 1983.

Michelsson, Michelsson; "Phonation In The Newborn, Infant Cry" 1999.

Pearce, Taylor; "Time–Frequency Analysis Of Infant Cry" Measures That Identify Indivudals 1993.

Copeland; "What To Listen For In Music" 1957, Chapter IV.

* cited by examiner

APPARATUS AND METHOD FOR PERFORMING MUSICAL PERCEPTION SOUND ANALYSIS ON A SYSTEM

This application claims the priority of U.S. Provisional Patent Application Serial No. 60/298,445 filed Jun. 15, 2001.

FIELD OF THE INVENTION

The present invention relates generally to analysis of living and non-living systems, and more particularly, to a system and method for analyzing systems using musical perception sound analysis.

BACKGROUND OF THE INVENTION

Living and non-living systems are complex. Analyzing, e.g., performing diagnostics, for complex systems can be complex and/or inaccurate. For example, the human body is an extremely complex living system. Modern medicine has provided diagnostic machinery capable of measuring, monitoring and displaying body parameters, such as blood pressure, heart beat, and brain waves.

However, in many situations, these parameters are simply indicators of the existence of the underlying problem. Trained medical personnel with vast experience working with similar patients become attuned to the sounds made by their patients. Based on their training and experiences, some of these medical personnel are able to correlate changes in the sounds the patients make with changes in their conditions. However, such knowledge is difficult to quantify and use with any degree of accuracy. Thus, it is also difficult to teach such knowledge to others.

The inventor has discovered a correlation between vibrations living and nonliving systems make in response to changes in their conditions. Quantified in musical terminology, these changes may be quantified, taught and used to train systems to perform system diagnostics.

The present invention is aimed at one or more of the problems identified above.

SUMMARY OF THE INVENTION AND ADVANTAGES

In one aspect of the present invention, an apparatus for analyzing a system using musical perception sound analysis is provided. The apparatus includes a transducer for receiving acoustic events generated by the system and an analysis module coupled to the transducer for receiving the acoustic events and for monitoring the system as a function of a set of musical perception parameters and responsively identifying a presence of a predetermined condition.

In another aspect of the present invention, an apparatus for determining a set of musical perception parameters of a system for use in performing musical perception sound analysis is provided. The apparatus includes a transducer for sensing acoustic energy of the system under a first condition and responsively generating a first acoustic event signal and for sensing acoustic energy of the system under a second condition and responsively generating a second acoustic event signal. The apparatus also includes an analog to digital converter and a computer-based analyzer. The analog to digital converter is coupled to the transducer and is adapted to receive the first and second acoustic event signals, digitize the first and second acoustic event signals, and responsively generate first and second acoustic digital signals. The computer-based analyzer is coupled to the analog to digital converter and is adapted to receive the first and second acoustic digital signals and to responsively generate first and second musical data signals and a graphic display of the first and second acoustic digital signals and/or the first and second musical data signals. The computer-based analyzer is adapted to assist a user in listening to the first and second acoustic digital signals and responsively identifying at least one aural event and in reviewing the graphic display corresponding to the at least one aural event and responsively determining the set of musical perception parameters.

In still another aspect of the present invention, a method for analyzing a system using musical perception sound analysis is provided. The method includes the steps of recording a first acoustic event of the system under a first condition and a second acoustic event of the system under a second condition and analyzing the first and second acoustic events and responsively determining a set of musical perception parameters. The method further includes the step of monitoring the system as a function of the set of musical perception parameters and responsively identifying a presence of the second condition.

In still one more aspect of the present invention, a method of determining a set of musical perception parameters of a system for use in performing musical perception sound analysis is provided. The method includes the steps of sensing acoustic energy of the system under a first condition and responsively generating a first acoustic event signal and sensing acoustic energy of the system under a second condition and responsively generating a second acoustic event signal. The method also includes the steps of receiving the first and second acoustic event signal, digitizing the first and second acoustic event signals, and responsively generating first and second acoustic digital signals and receiving the first and second acoustic digital signals and responsively generating first and second musical data signals. The method further includes the steps of receiving the first and second acoustic digital signals and the first and second musical data signals and generating a graphic display of the signals, listening to the first and second acoustic digital signals and responsively identifying at least one aural event, and reviewing the graphic display of the signals corresponding to the at least one aural event and determining the set of musical perception parameters.

BRIEF DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE PREFERRED EMBODIMENT

With reference to the Figs., and in operation, the present invention provides an apparatus and method for analyzing a system using musical perception sound analysis. The analysis of the system is used to determine the presence of a predetermined condition or conditions. In practice, the apparatus and method is used in two modes. In the first or training mode, the apparatus and method is used to determine a set of musical perception parameters which may then be used in the second mode to detect the presence of the predetermined condition or conditions.

The apparatus and method may be used with living and non-living systems. For example, the apparatus and method may be used to detect the presence of certain stimuli to newborn babies. Such stimuli could include pain, the administration of a drug, or distress, such as breathing difficulty or an irregular heartbeat. In another example, the system and method may be used to detect the presence of certain conditions in a mechanical machine such as an automobile engine.

In one embodiment, a user operates the apparatus to determine the set of musical perception parameters. The user is preferably a music expert. In another embodiment, the system automatically determines the set of musical perception parameters.

Figure 1:
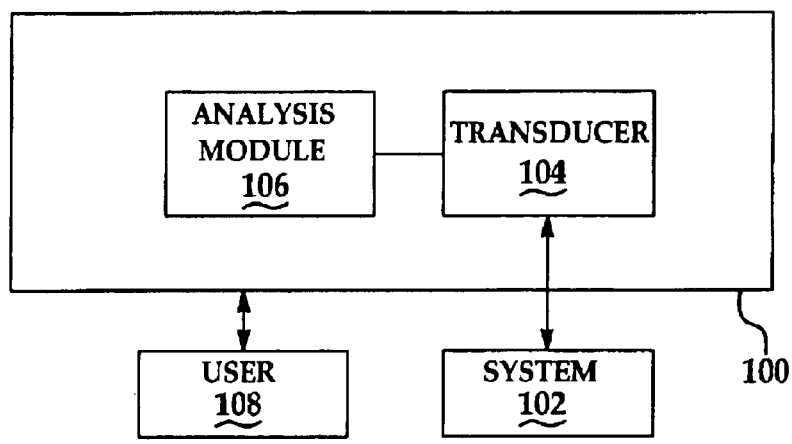
FIG. 1 is a block diagram of an apparatus for analyzing a system using musical perception sound analysis, according to an embodiment of the present invention.

With specific reference to FIG. 1, an apparatus 100 for analyzing a system 102 using musical perception sound analysis according to an embodiment of the present invention will now be described. The apparatus 100 includes a transducer 104, e.g., an omnidirectional microphone, for receiving acoustic events, i.e., oscillations, generated by the system 102. It should be noted that acoustic events are defined as oscillations in regular or irregular patterns that may or may not be detectable by the human ear. For example, acoustic events includes sounds, magnetic frequencies, ultrasonic and subsonic frequencies, as well as light frequencies. An analysis module 106 is coupled to the transducer 104. The analysis module 106 receives the acoustic events, monitors the system 102 as a function of the set of musical perception parameters and responsively identifies a presence of a predetermined condition. The musical perception parameters include a set of musical variables, changes in the musical variables, and/or relationships between the musical variables. The musical perception parameters includes a set of musical variables and may also include changes in the musical variables, and/or relationships between the musical variables. Preferably, the musical variables include rhythm and melody. Rhythm includes attack, decay, cessation and amplitude. Melody includes pitch, timbre, and amplitude.

In one embodiment, the analysis module 106 analyzes the acoustic events against a developed syntax. Preferably, the syntax is defined in terms of rhythm and melody. Acoustic events include sounds, magnetic frequencies, ultrasonic and subsonic frequencies, as well as light frequencies.

In one embodiment rhythm is defined as including patterns of attack, decay, and cessation. In another embodiment, rhythm is defined as including patterns of attack, decay, cessation and amplitude.

In one embodiment, melody is defined as including patterns of pitch and timbre. In another embodiment, melody is defined as including patterns of pitch, timbre, and amplitude. Timbre is defined by the harmonic spectrum.

As discussed above, the analysis module 106 is operated by a user 108 during a training mode to determine the set of musical perception parameters which will be used by the apparatus 100 and method to detect the presence of one or more predetermined conditions. During the training mode, the transducer 104 is adapted to receive a first acoustic event or sound and a second acoustic event. The first acoustic event is generated by the system 102 under a first condition and the second acoustic event being generated by the system 102 under a second condition. During the training mode, the first and second acoustic events may be pre-recorded, generated by a test system (not shown), and/or generated during experimental trials.

For a given stimuli, for example, pain, the first condition is the absence of the stimuli and the second condition is the presence of the stimuli. By listening to the first and second acoustic events, under the first and second conditions, respectively, the user, using his or her musical expertise detects an aural event in either of the first and second acoustic event. The user's expertise is used to determine that the aural event is a result of the presence of the second condition.

The user 108, through analysis of the aural event, determines the set of musical perception parameters as a function of the aural event. The apparatus is then trained or programmed to monitor the system 102 to detect the occurrence or presence of the musical perception parameters during a non-training mode.

Figure 2:
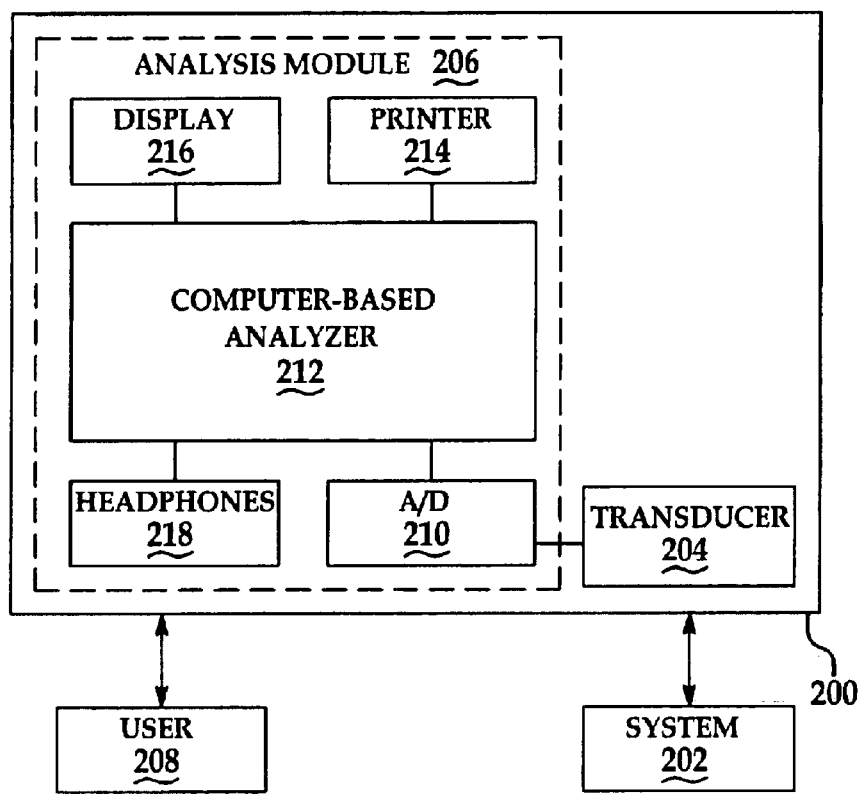
FIG. 2 is a block diagram of an apparatus for analyzing a system using musical perception sound analysis, according to another embodiment of the present invention.

With reference to FIG. 2, an apparatus 200 for analyzing a system 202 using musical perception sound analysis, according to a second embodiment of the present invention, will now be discussed.

A transducer 204 records a first acoustic event generated by the system in a training mode under a first condition and a second acoustic event generated by the system in the training mode under a second condition and responsively generating first and second acoustic signals. The transducer 204 also records an actual acoustic event generated by the system in a non-training mode and responsively generating an actual acoustic event signal.

An analysis module 206 is coupled to the transducer 204 and receives the first, second and actual acoustic event signals and converts the first, second and actual acoustic events signals into first, second, and third acoustic digital signals, respectively. The analysis module 206 generates a graphic display of the first, second, and third digital signals, and for monitors the system 202 as a function of a set of musical perception parameters and responsively identifies a presence of a predetermined condition.

The analysis module 206 is adapted to assist a user 208 in the training mode, to analyze the first and second acoustic event signals and the graphic display, detect an aural event, and responsively determine the musical perception parameters.

The transducer 204 is preferably an omnidirectional microphone coupled to an analog to digital (A/D) converter 210. The A/D converter 210 converts the first, second and actual acoustic event signals into first, second, and third acoustic digital signals. The digital signals are then delivered to a computer-based analyzer 212. Preferably, the computer-based analyzer 212 is a personal computer, such as a Pentium IV based personal computer with an operating speed of 1.4 GHz.

A recorder (not shown) may also be used to archive the digital data. The recorder is coupled between the A/D converter 210 and the analyzer 212. Preferably, a digital encoding format with a 32 bit word length at a sampling rate of 192 kHz is used.

The analysis module 206 includes a printer 214 and a display 216 (such as video monitor). The graphic display may be printed on the printer 214 and/or shown on the display 216. The graphic display is one of a wave, sonographic, or spectrographic graphs. One or more of these may be utilized.

The user may listen to the digital signals through speakers or a pair of electrostatic headphones 218. A graphical user interface (not shown) running on the computer-based analyzer 212 allows the operator to control the analysis modules 206 in order to listen to the digital signals, view the graphs, and to focus and expand on a particular portion of the signals and expand the graphs to this portion.

In one embodiment, the computer-based analyzer 212 includes a musical notation software module (not shown) which receives the first and second acoustic digital signals and converts the acoustic digital signals into first and second musical data signals. The first and second musical data signals may then be displayed on the printer 214 and/or the display 216 in musical notation. Preferably, the musical notation software module is based on the Musical Instrument Digital Interface (MIDI) protocol.

The first and second musical data signals are represented in staves. The stave contain cleft signs depicting the relative frequency range contained within each staff. Time signatures denote the ration of a standard durational unit and their relative groupings. A key signature denotes the pitch center, i.e., the most iterated note. Duration is plotted using a system in which a whole note equals 4, a dotted half note equals 3, a quarter note equals 2, an eighth note equals 0.5, and a sixteenth note equals 0.25 of a second. The respective shape of the note heads are assigned to respective sound events in an individualized manner: normal note heads represent pure pitch and percussive note heads will denote non-definitive pitch sounds.

Dynamic markings are used to depict specific changes and trends in amplitude. Other specialized markings may be used to depict modulations in amplitude, frequency, and duration, as well as attack and decay.

In one embodiment, the computer-based analyzer 212 includes a wave editor software module (not shown) which received the first and second acoustic digital signals and generates a wave graph of the signals for printing on the printer 214 and/or viewing on the display 216.

In the discussed embodiments, training of the analysis module 106 and identification/determination of the musical perception parameters is accomplished by a musical expert through operation of the analysis module 106 in a training mode. However, this portion of the operation analysis module 106 could also be performed by expert software.

The computer-based analyzer 212 is adapted to assist the user 208 in listening to the first and second acoustic digital signals and responsively identifying at least one aural event and in reviewing the graphic display (from the printer 214 or the display 216) corresponding to the at least one aural event and responsively determining the set of musical perception parameters.

Figure 3:
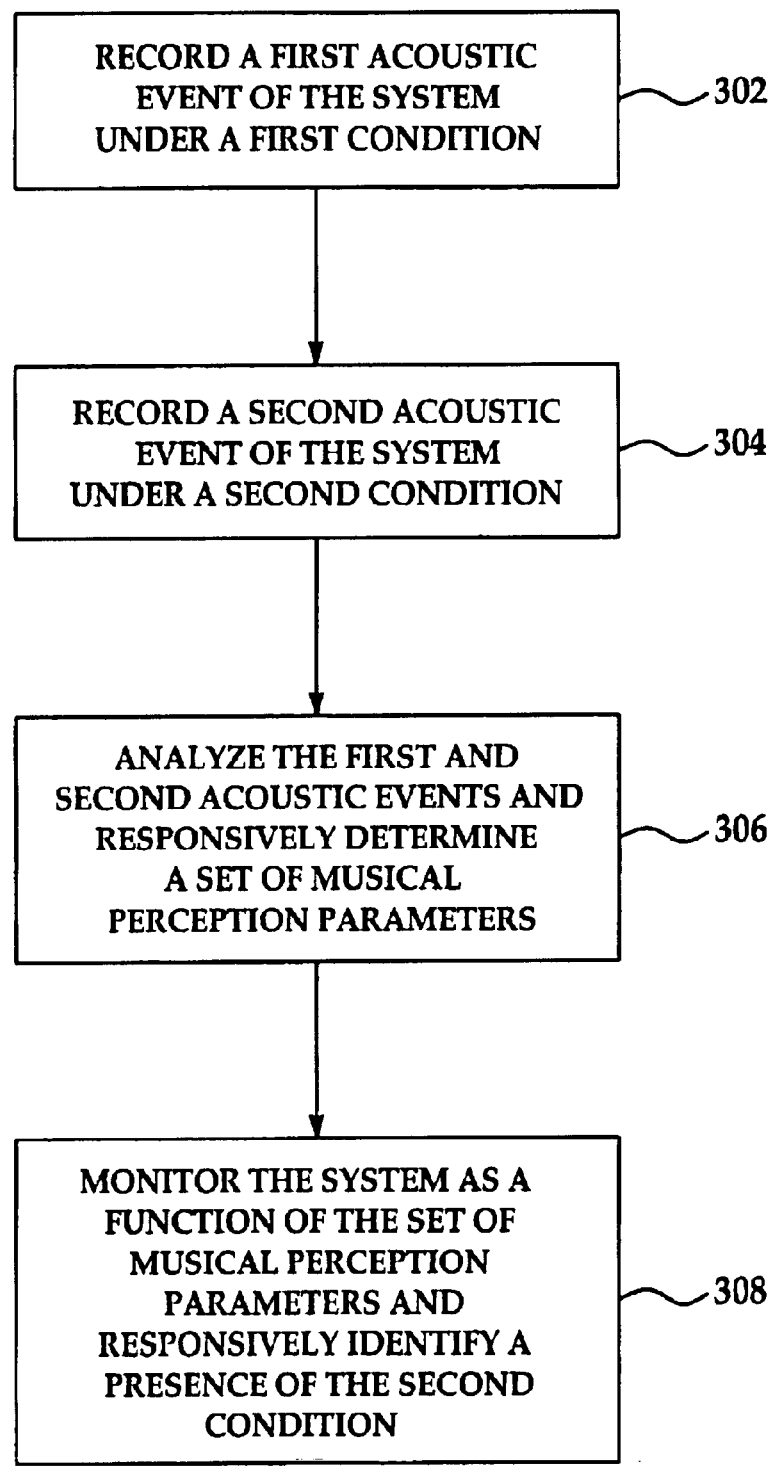
FIG. 3 is a flow diagram of a method for analyzing a system using musical perception sound analysis, according to an embodiment of the present invention.

With reference to FIG. 3, a method for analyzing a system using musical perception sound analysis, according to an embodiment of the present invention will now be discussed.

In a first control block 302, a first acoustic event of the system under a first condition is recorded. In a second control block 304, a second acoustic event of the system under a second condition is recorded. In a third control block 306, the first and second acoustic events are analyzed and a set of musical perception parameters are responsively determined. In a fourth control block 308, the system is monitored as a function of the set of musical perception parameters and a presence of the second condition is responsively identified.

Figure 4:
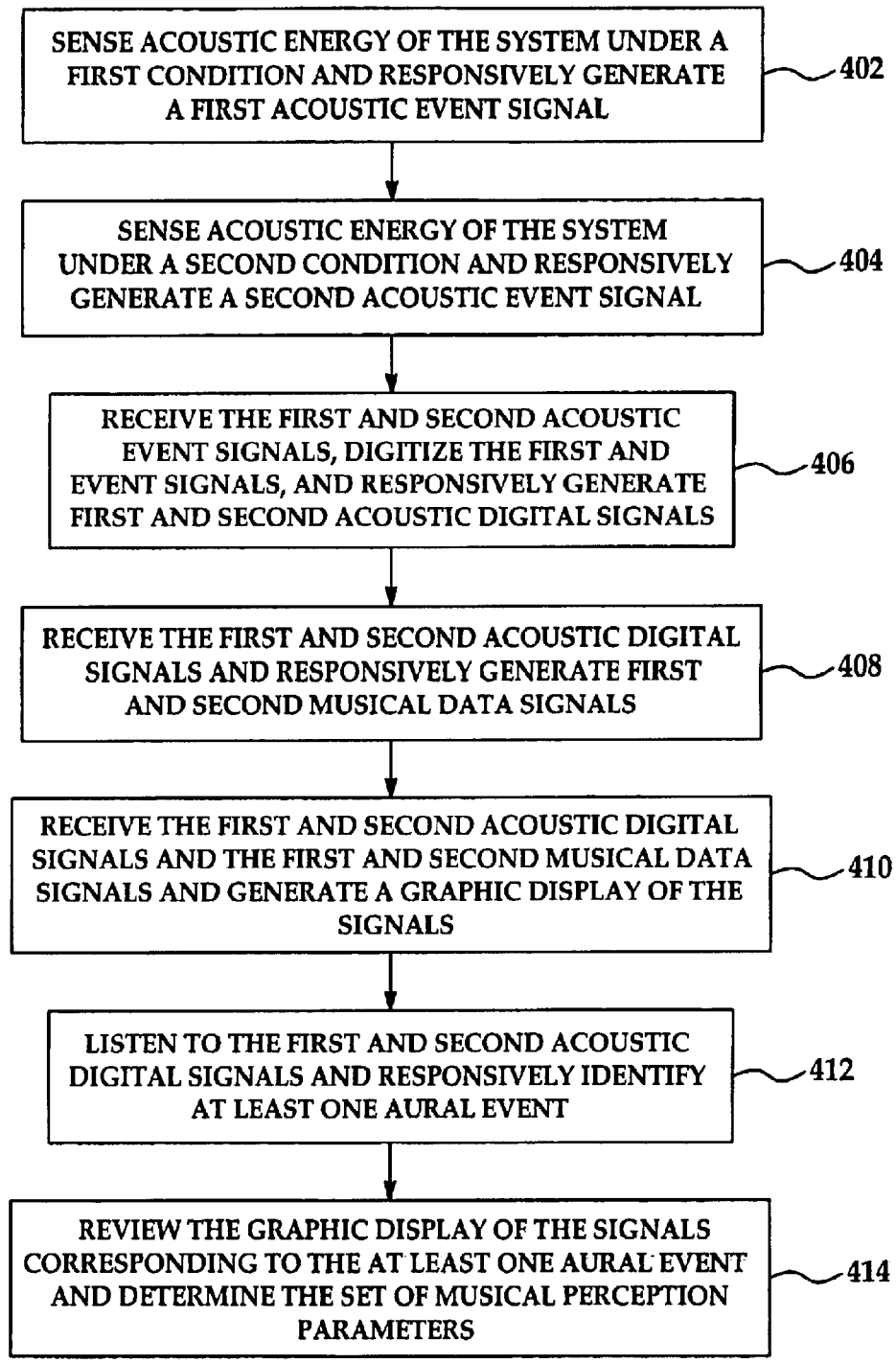
FIG. 4 is a flow diagram of a method for analyzing a system using musical perception sound analysis, according to an embodiment of the present invention.

With reference to FIG. 4, a method for analyzing a system using musical perception sound analysis, according to another embodiment of the present invention will now be discussed.

In a fifth control block 402, acoustic energy of the system under a first condition sensed and a first acoustic event signal is responsively generated. In a sixth control block 404, acoustic energy of the system under a second condition is sensed and a second acoustic event signal is responsively generated.

In a seventh control block 406, the first and second acoustic event signals are received and digitized, and first and second acoustic digital signals are responsively digitized. In an eighth control block 408, the first and second acoustic digital signals are received and first and second musical data signals are responsively generated.

In a ninth control block 410, the first and second acoustic digital signals and the first and second musical data signals are received and a graphic display of the signals is generated. In a tenth control block 412, a user listens to the first and second acoustic digital signals and responsively identifies at least one aural event.

In an eleventh control block 412, the graphic display of the signals is corresponding to the at least one aural event is reviewed and the set of musical perception parameters is determined.

As discussed above, the computer-based analyzer 212 generates graphs which are used by the user 108,208 to assist the user in analyzing the aural events present in an acoustic event signals. An aural event is a feature of the event signal which the user determines corresponds to the predetermined condition. Thus, by analyzing the aural event and determining a set of musical perception parameters which describe the aural event, the system can be monitored for these parameters and the predetermined condition can be detected.

Figure 5A:
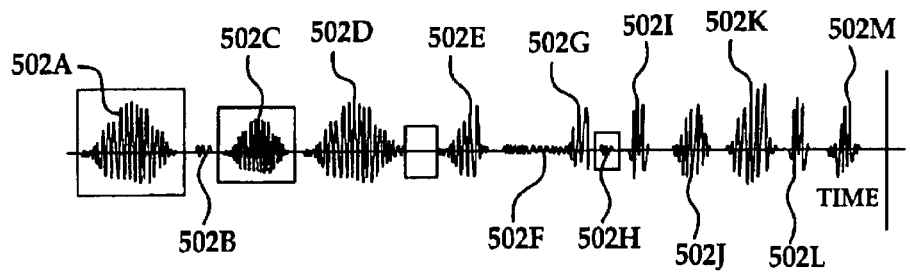
FIG. 5A is a wave graph of a series of acoustic events.
Figure 5B:
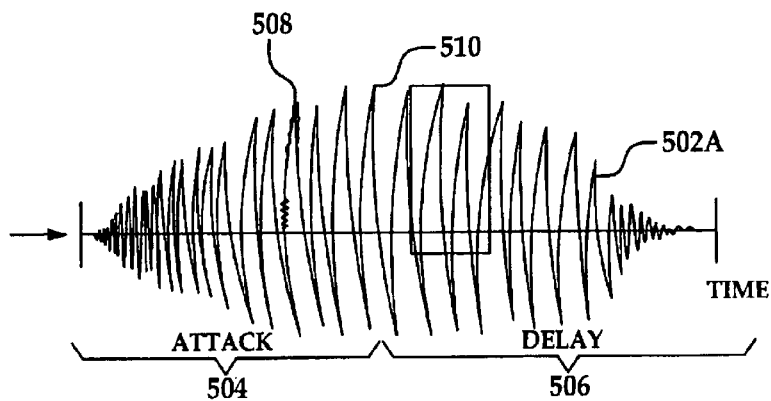
FIG. 5B is an expanded wave graph of one of the acoustic events of FIG. 5.
Figure 8A:
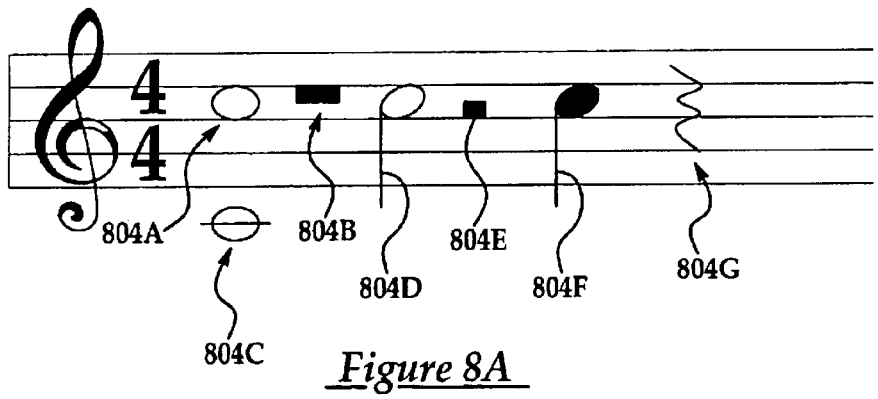
FIG. 8A represents a first series of exemplary acoustic events in musical notation.

With reference to FIGS. 5A and 5B, a wave graph of an exemplary acoustic signal (or wave signal) 500 is shown. The wave signal 500 is shown with first through thirteenth acoustic events 501A–502M. The acoustic events 502A–502M are separated by an absence of sound. The wave editor software module allows the user 108,208 to "zoom" in on a portion of the wave signal 500. A portion of the wave signal 500 is shown in FIG. 5A. This portion includes the first acoustic event 502A. The first acoustic event 502A has a generally triangular waveform with an attack portion 504 and a decay portion 506. The jagged edges, e.g., at point 508, are indicative of odd harmonics. The point of the acoustic event 502A with the largest amplitude is at point 510. The total time of the acoustic event 502A is the attack time plus the decay time.

Figure 6:
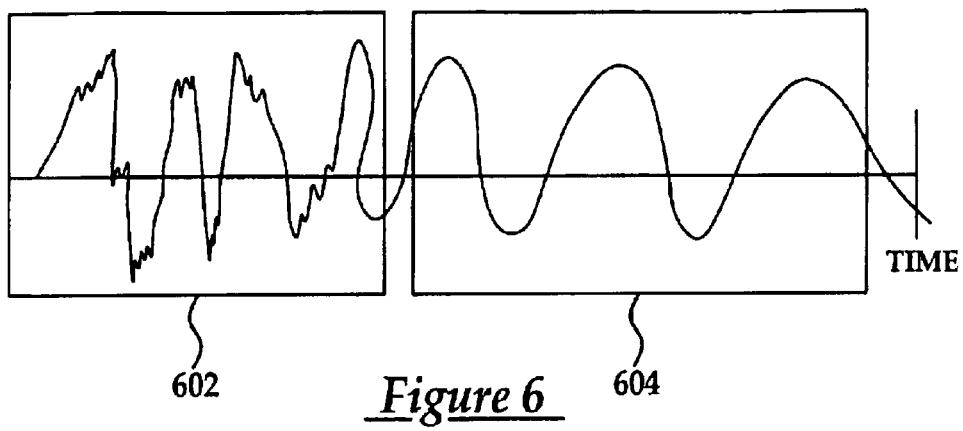
FIG. 6 is a wave graph having a first portion and a second portion.

Another exemplary acoustic signal or wave signal 600 is shown in FIG. 6. A first portion 602 of the wave signal 600, as illustrated by the jagged edges and irregular waveform includes odd harmonics and dysphonation. The first portion 602 of the wave signal 600 could be a mix of a sine wave, a square wave, a triangle wave, a sawtooth wave, and/or a pulse wave.

Figure 7A:
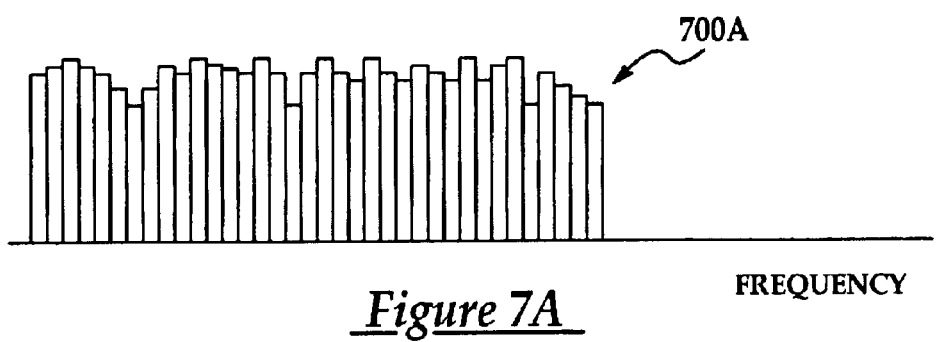
FIG. 7A is a spectrographic of an exemplary acoustic event.
Figure 7B:
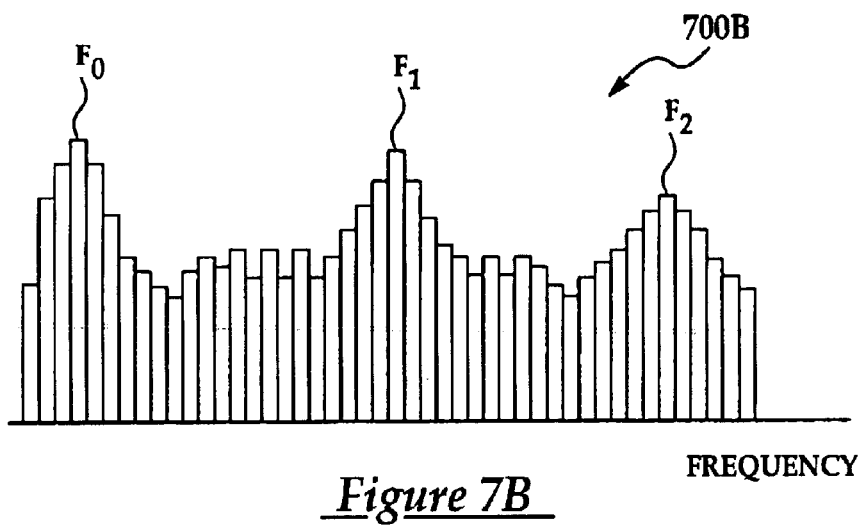
FIG. 7B is a spectrographic of another exemplary acoustic event.

With reference to FIGS. 7A and 7B, two exemplary spectrographics 700A, 700B are shown. The first spectrographic 700A illustrates an acoustic event with a harsh timbre and thus has a mix of even and odd harmonics. The second spectrographic 700B illustrates an acoustic even with a more pure tone and thus, the harmonics ($F_1$ and $F_2$) are more clearly represented.

With reference to FIGS. 8A–8E, several acoustic events are illustrated in musical notation. With specific reference to 8A, a first musical score 802 includes symbols representing a series of acoustic events 804A–804G. First and second acoustic events 804A, 804B are comprised sounds of a long duration with a relatively high pitch and a lower pitch, respectively. A first rest symbol 804C represents a rest, i.e., no sound, having the same duration as a whole note. The third acoustic event 804D is comprised of a sound having a duration equal to ½ a whole note. A second rest symbol 804E represents a half rest. A fourth acoustic event 804F represents a sound having a duration equal to ¼ a whole note. A third rest symbol 804G represents a quarter rest.

Figure 8B:
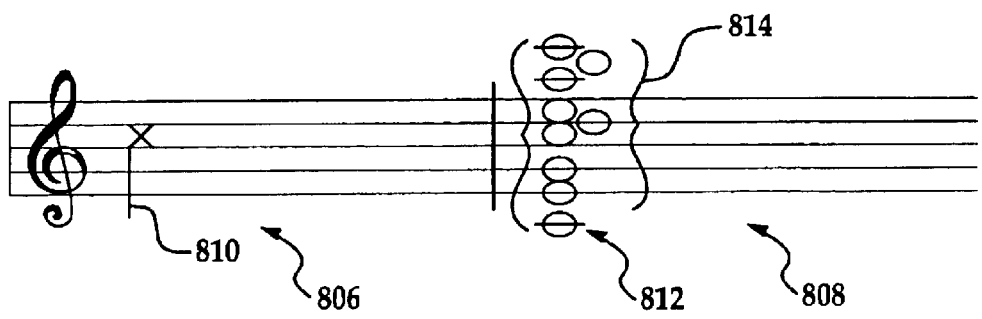
FIG. 8B represents a second series of exemplary acoustic events in musical notation.

With specific reference to FIG. 8B, fifth and sixth acoustic events 806, 808 are shown. The fifth acoustic event 806 includes a note 810 representing a percussion sound, such as a cough. The sixth acoustic event 808 is an event with spectral harmony. The event 808 includes a note 812 which represents a fundamental frequency and a series of notes 814 which represent harmonics, e.g., $F_1$–$F_{17}$, of the fundamental frequency.

Figure 8C:
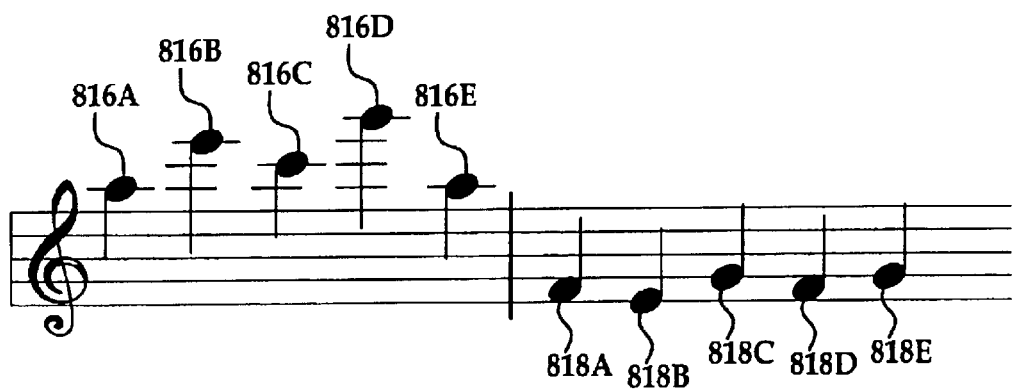
FIG. 8C represents a third series of exemplary acoustic events in musical notation.

With specific reference to FIG. 8C, the first five notes 816A, 816B, 816C, 816D, 816E represent acoustic events with relatively high pitches. Acoustic events with relatively high pitches have more energy. The second five notes 818A, 818B, 818C, 818D, 818E represent acoustic events with lower pitches, and thus, have less energy.

Figure 8D:
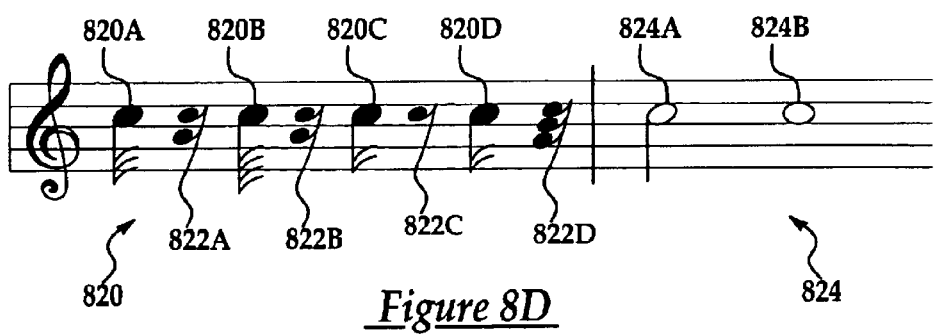
FIG. 8D represents a fourth series of exemplary acoustic events in musical notation; and, FIG. 8E represents a fifth series of exemplary acoustic events in musical notation.

With specific reference to FIG. 8D, a first portion 820 of includes four notes 820A, 820B, 820C, 820D, each followed by a rest 822A, 822B, 822C, 822D. The second portion 824 includes two sound events (represented by two notes 824A, 824B) of longer duration. The first portion 820 with has more energy than the second portion 824.

Figure 8E:
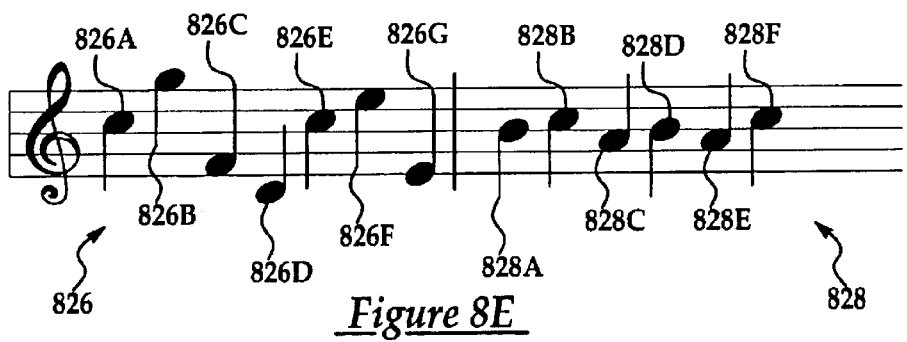

With specific reference to FIG. 8E, a first portion 826 includes a plurality of acoustic events 826A, 826B, 826C, 826D, 826E, 826F, 826G. A second portion 828 includes a plurality of acoustic events 828A, 828B, 828C, 828D, 828E, 828F. The difference in pitch between the acoustic events 826A, 826B, 826C, 826D, 826E, 826F, 826G in the first portion 826 is greater than the difference in pitch between the acoustic events 828A, 828B, 828C, 828D, 828E, 828F in the second portion 828. Thus, there is more energy in the first portion 826 than in the second portion 828.

Obviously, many modifications and variations of the present invention are possible in light of the above teachings.

What is claimed is:

1. An apparatus for analyzing a system using musical perception sound analysis, comprising:
   a transducer for receiving acoustic events generated by the system;
   an analysis module coupled to the transducer for receiving the acoustic events and for monitoring the system as a function of a set of musical perception parameters and responsively identifying a presence of a predetermined condition as a function of the musical perception parameters.

2. An apparatus, as set forth in claim 1, wherein the analysis module analyzes the acoustic events against a developed syntax.

3. An apparatus, as set forth in claim 2, wherein the syntax is defined in terms of rhythm and melody.

4. An apparatus, as set forth in claim 1, wherein the musical perception parameters includes a set of musical variables, changes in the musical variables, and/or relationships between the musical variables.

5. An apparatus, as set forth in claim 4, wherein the set of musical variables includes at least one of rhythm and melody.

6. An apparatus, as set forth in claim 5, wherein rhythm includes patterns of attack, decay, and cessation.

7. An apparatus, as set forth in claim 5, wherein rhythm includes patterns of attack, decay, cessation, and amplitude.

8. An apparatus, as set forth in claim 5, wherein melody includes patterns of pitch and timbre.

9. An apparatus, as set forth in claim 5, wherein melody includes patterns of pitch, timbre, and amplitude.

10. An apparatus, as set forth in claim 1, wherein the analysis module analyzes the acoustic events against a developed syntax defined in terms of rhythm and melody, wherein rhythm includes patterns of attack, decay, and cessation, and melody includes patterns of pitch and timbre.

11. An apparatus, as in claim 10, wherein the acoustic events are primarily analyzed in terms of rhythm and secondarily analyzed in terms of melody.

12. An apparatus, as in claim 10, wherein the acoustic events are primarily analyzed in terms of melody and secondarily analyzed in terms of rhythm.

13. An apparatus, as set forth in claim 1, wherein the system is a living system.

14. An apparatus, as set forth in claim 1, wherein the system is a non-living system.

15. An apparatus, as set forth in claim 1, wherein the analysis module is trained by a user, the analysis module being adapted to assist the user in detecting an aural event and determining the set of musical perception parameters as a function of the aural event.

16. An apparatus, as set forth in claim 15, wherein the transducer is adapted to receive a first acoustic event and a second acoustic event, the first acoustic event being generated by the system under a first condition and the second acoustic event being generated by the system under a second condition.

17. An apparatus, as set forth in claim 16, wherein the second condition is the presence of a stimuli and the first condition is the absence of the stimuli.

18. An apparatus, as set forth in claim 17, wherein the stimuli is pain.

19. An apparatus, as set forth in claim 17, wherein the stimuli is a drug administered to the system.

20. An apparatus, as set forth in claim 16, wherein the second condition is the predetermined condition.

21. An apparatus, as set forth in claim 15, wherein the user is a music expert.

22. An apparatus, as set forth in claim 16, wherein the analysis module is adapted to generate a sonogram of at least one of the first and second acoustic events.

23. An apparatus, as set forth in claim 16, wherein the analysis module is adapted to generate a spectrograph of at least one of the first and second acoustic events.

24. An apparatus, as set forth in claim 16, wherein the apparatus is adapted to convert at least one of the first and second acoustic events into musical notation.

25. An apparatus for analyzing a system using musical perception sound analysis, comprising:
- a transducer for recording a first acoustic event generated by the system in a training mode under a first condition, a second acoustic event generated by the system in the training mode under a second condition, and an actual acoustic event generated by the system in a non-training mode; and,
- an analysis module coupled to the transducer for receiving the first, second and actual acoustic events and monitoring the system as a function of a set of musical perception parameters and responsively identifying a presence of a predetermined condition of the system, wherein the analysis module is adapted to assist a user in the training mode, to analyze the first and second acoustic events, detect an aural event, and responsively determine the musical perception parameters, the predetermined condition being defined by the musical perception parameters.

26. An apparatus, as set forth in claim 25, wherein the analysis module analyzes the acoustic events against a developed syntax.

27. An apparatus, as set forth in claim 26, wherein the syntax is defined in terms of rhythm and melody.

28. An apparatus, as set forth in claim 25, wherein the musical perception parameters includes a set of musical variables, changes in the musical variables, and/or relationships between the musical variables.

29. An apparatus, as set forth in claim 28, wherein the set of musical variables includes at least one of rhythm and melody.

30. An apparatus, as set forth in claim 29, wherein rhythm includes patterns of attack, decay, and cessation.

31. An apparatus, as set forth in claim 29, wherein rhythm includes patterns of attack, decay, cessation, and amplitude.

32. An apparatus, as set forth in claim 29, wherein melody includes patterns of pitch and timbre.

33. An apparatus, as set forth in claim 29, herein melody includes patterns of pitch, timbre, and amplitude.

34. An apparatus, as set forth in claim 25, wherein the analysis module analyzes the acoustic events against a developed syntax defined in terms of rhythm and melody, wherein rhythm includes patterns of attack, decay, and cessation, and melody includes patterns of pitch and timbre.

35. An apparatus, as in claim 34, wherein the acoustic events are primarily analyzed in terms of rhythm an d secondarily analyzed in terms of melody.

36. An apparatus, as in claim 34, wherein the acoustic events are primarily analyzed in terms of melody and secondarily analyzed in terms of rhythm.

37. An apparatus, as set forth in claim 25, herein the musical perception parameters includes a set of musical variables, changes in the musical variables, and relationships between the variables.

38. An apparatus, as set forth in claim 37, wherein the set of musical variables includes at least one of pitch and melody.

39. An apparatus, as set forth in claim 38, wherein rhythm includes attack, decay, cessation and decibel range.

40. An apparatus, as set forth in claim 38, wherein melody includes pitch, pitch intervals, highest pitch, lowest pitch, timbre, contour, and decibel range.

41. An apparatus, as set forth in claim 37, wherein the set of musical variables includes pitch and melody.

42. An apparatus, as set forth in claim 41, wherein rhythm includes attack, decay, cessation and decibel range.

43. An apparatus, as set forth in claim 41, wherein melody includes pitch, pitch intervals, highest pitch, lowest pitch, timbre, contour, and decibel range.

44. An apparatus, as set forth in claim 25, wherein the system is a living system.

45. An apparatus, as set forth in claim 25, wherein the system is a non-living system.

46. An apparatus, as set forth in claim 25, wherein the second condition is the presence of a stimuli and the first condition is the absence of the stimuli.

47. An apparatus, as set forth in claim 46, wherein the stimuli is pain.

48. An apparatus, as set forth in claim 46, wherein the stimuli is a drug administered to the system.

49. An apparatus, as set forth in claim 25, wherein the user is a music expert.

50. An apparatus, as set forth in claim 25, wherein the analysis module is adapted to generate a sonogram of at least one of the first and second acoustic events in the training mode.

51. An apparatus, as set forth in claim 25, wherein the analysis module is adapted to generate a spectrograph of at least one of the first and second acoustic events in the training mode.

52. An apparatus, as set forth in claim 25, wherein the analysis module is adapted to convert at least one of the first and second acoustic events into musical notation.

53. An apparatus for analyzing a system using musical perception sound analysis, comprising:
- a transducer for recording a first acoustic event generated by the system in a training mode under a first condition and a second acoustic event generated by the system in the training mode under a second condition and responsively generating first and second acoustic event signals, and for recording an actual acoustic event generated by the system in a non-training mode and responsively generating an actual acoustic event signal; and,
- an analysis module coupled to the transducer for receiving the first, second and actual acoustic event signals and converting the first, second and actual acoustic event signals into first, second, and third acoustic digital signals, respectively, for generating a graphic display of the first, second, and third acoustic digital signals, and for monitoring the system as a function of a set of musical perception parameters and responsively identifying a presence of a predetermined condition of the system, wherein the analysis module is adapted to assist a user in the training mode, to analyze the first and second acoustic event signals and the graphic display, detect an aural event, and responsively determine the musical perception parameters, the predetermined condition being defined by the musical perception parameters.

54. An apparatus, as set forth in claim 53, wherein the analysis module analyzes the acoustic events against a developed syntax defined in terms of rhythm and melody, wherein rhythm includes patterns of attack, decay, and cessation, and melody includes patterns of pitch and timbre.

55. An apparatus, as set forth in claim 53, wherein the set of musical perception parameters include a set of musical variables, changes in the musical variables, and relationships between the variables.

56. An apparatus, as set forth in claim 53, wherein the graphic display is one of a wave, sonographic, or spectrographic graphs.

57. An apparatus for determining a set of musical perception parameters of a system for use in performing musical perception sound analysis, comprising:
- a transducer for sensing acoustic energy of the system under a first condition and responsively generating a first: acoustic event signal and for sensing acoustic energy of the system under a second condition and responsively generating a second acoustic event signal;
- an analog to digital converter coupled to the transducer and being adapted to receive the first and second acoustic event signals, digitize the first and second acoustic event signals, and responsively generate first and second acoustic digital signals;
- a computer-based analyzer coupled to the analog to digital converter and being adapted to receive the first and second acoustic digital signals and to responsively generate first and second musical data signals and a graphic display of the first and second acoustic digital signals and/or the first and second musical data signals, wherein the computer-based analyzer is adapted to assist a user in listening to the first and second acoustic digital signals and responsively identifying at least one aural event and in reviewing the graphic display corresponding to the at least one aural event and responsively determining the set of musical perception parameters, the at least one aural event resulting from the second condition.

58. An apparatus, as set forth in claim 57, wherein the analysis module analyzes the acoustic events against a developed syntax defined in terms of rhythm and melody, wherein rhythm includes patterns of attack, decay, and cessation, and melody includes patterns of pitch and timbre.

59. An apparatus, as set forth in claim 57, wherein the musical perception parameters includes a set of musical variables, changes in the musical variables, and relationships between the variables.

60. An apparatus, as set forth in claim 59, wherein the musical variables include melody and rhythm.

61. An apparatus, as set forth in claim 57, wherein the graphic display is one of a wave, sonographic, or spectrographic graphs of the first and second acoustic digital signals.

62. An apparatus, as set forth in claim 57, wherein the graphic display is a representation of the first and second musical data signals in musical notation.

63. A method for analyzing a system using musical perception sound analysis, including the steps of:
- recording a first acoustic event of the system under a first condition;
- recording a second acoustic event of the system under a second condition;
- analyzing the first and second acoustic events and responsively determining a set of musical perception parameters; and,
- monitoring the system as a function of the set of musical perception parameters and responsively identifying a presence of the second condition as a function of the musical perception parameters.

64. A method, as set forth in claim 63, including the step of analyzing the acoustic events against a developed syntax.

65. A method, as set forth in claim 64, wherein the syntax is defined in terms of rhythm and melody.

66. A method, as set forth in claim 63, wherein the musical perception parameters includes a set of musical variables, changes in the musical variables, and/or relationships between the musical variables.

67. A method, as set forth in claim 66, wherein the set of musical variables includes at least one of rhythm and melody.

68. A method, as set forth in claim 67, wherein rhythm includes patterns of attack, decay, and cessation.

69. A method, as set forth in claim 67, wherein rhythm includes patterns of attack, decay, cessation, and amplitude.

70. A method, as set forth in claim 67, wherein melody includes patterns of pitch and timbre.

71. A method, as set forth in claim 67, wherein melody includes patterns of pitch, timbre, and amplitude.

72. A method, as set forth in claim 63, wherein the analysis module analyzes the acoustic events against a developed syntax defined in terms of rhythm and melody, wherein rhythm includes patterns of attack, decay, and cessation, and melody includes patterns of pitch and timbre.

73. A method, as in claim 72, wherein the acoustic events are primarily analyzed in terms of rhythm and secondarily analyzed in terms of melody.

74. A method, as in claim 72, wherein the acoustic events are primarily analyzed in terms of melody and secondarily analyzed in terms of rhythm.

75. A method, as set forth in claim 63, wherein the system is a living system.

76. A method, as set forth in claim 63, wherein the system is a non-living system.

77. A method, as set forth in claim 63, wherein the second condition is the presence of a stimuli and the first condition is the absence of the stimuli.

78. A method, as set forth in claim 77, wherein the stimuli is pain.

79. A method, as set forth in claim 77, wherein the stimuli is a drug administered to the system.

80. A method, as set forth in claim 63, wherein the step of analyzing the first and second acoustic events includes the step of detecting an aural event.

81. A method, as set forth in claim 80, wherein the set of musical perception parameters is determined as a function of the aural event.

82. A method, as set forth in claim 63, wherein the step of analyzing the first and second acoustic events and responsively determining a set of musical perception parameters is performed by a music expert.

83. A method, as set forth in claim 82, wherein the step of analyzing the first and second acoustic events includes the step of detecting an aural event.

84. A method, as set forth in claim 82, including the step of generating a sonogram of at least one of the first and second acoustic events.

85. A method, as set forth in claim 82, including the step of generating a spectrograph of at least one of the first and second acoustic events.

86. A method, as set forth in claim 82, including the step of converting at least one of the first and second acoustic events into musical notation.

87. A method for analyzing a system using musical perception sound analysis, including the steps of:
- recording a first acoustic event of the system under a first condition;
- recording a second acoustic event of the system under a second condition;
- analyzing the first and second acoustic events, detecting an aural event, and responsively determining a set of musical perception parameters, the musical perception parameters including a set of musical variables, changes in the musical variables, and relationships between the variables;

monitoring the system as a function of the set of musical perception parameters and responsively identifying a presence of the second condition as a function of the musical perception parameters.

88. A method, as set forth in claim 87, including the step of analyzing the acoustic events against a developed syntax defined in terms of rhythm and melody, wherein rhythm includes patterns of attack, decay, and cessation, and melody includes patterns of pitch and timbre.

89. A method, as set forth in claim 87, wherein the system is a living system.

90. A method, as set forth in claim 87, wherein the system is a non-living system.

91. A method, as set forth in claim 87, wherein the second condition is the presence of a stimuli and the first condition is the absence of the stimuli.

92. A method, as set forth in claim 87, wherein the stimuli is pain.

93. A method, as set forth in claim 87, wherein the stimuli is a drug administered to the system.

94. A method, as set forth in claim 87, wherein the step of analyzing the first and second acoustic events is performed by a music expert.

95. A method, as set forth in claim 94, including the step of generating a sonogram of at least one of the first and second acoustic events.

96. A method, as set forth in claim 94, including the step of generating a spectrograph of at least one of the first and second acoustic events.

97. A method, as set forth in claim 94, including the step of converting at least one of the first and second acoustic events into musical notation.

98. A method for analyzing a system using musical perception sound analysis, including the steps of:
   recording a first acoustic event of the system under a first condition and a second acoustic event of the system under a second condition and responsively generating first and second acoustic event signals;
   converting the first and second acoustic event signals into first and second acoustic digital signals;
   generating a graphic display of the first and second acoustic digital signals;
   listening to the first and second acoustic event signals and viewing the graphic display and responsively determining a set of musical perception parameters, the musical perception parameters including a set of musical variables, changes in the musical variables, and relationships between the variables; and, monitoring the system as a function of the set of musical perception parameters and responsively identifying a presence of the second condition as a function of the musical perception parameters.

99. A method, as set forth in claim 98, including the step of analyzing the acoustic events against a developed syntax defined in terms of rhythm and melody, wherein rhythm includes patterns of attack, decay, and cessation, and melody includes patterns of pitch and timbre.

100. A method, as set forth in claim 98, wherein the step of generating a graphic display includes the step of generating at least one of a wave, sonographic, and spectrographic graphs.

101. A method of determining a set of musical perception parameters of a system for use in performing musical perception sound analysis, including the steps of:
   sensing acoustic energy of the system under a first condition and responsively generating a first acoustic event signal;
   sensing acoustic energy of the system under a second condition and responsively generating a second acoustic event signal;
   receiving the first and second acoustic event signals digitizing the first and second acoustic event signals, and responsively generating first and second acoustic digital signals;
   receiving the first and second acoustic digital signals and responsively generating first and second musical data signals;
   receiving the first and second acoustic digital signals and the first and second musical data signals and generating a graphic display of the signals;
   listening to the first and second acoustic digital signals and responsively identifying at least one aural event; and,
   reviewing the graphic display of the signals corresponding to the at least one aural event and determining the set of musical perception parameters corresponding to the at least one aural event, the at least one aural event resulting from the second condition.

102. A method, as set forth in claim 101, including the step of analyzing the acoustic events against a developed syntax defined in terms of rhythm and melody, wherein rhythm includes patterns of attack, decay, and cessation, and melody includes patterns of pitch and timbre.

103. A method, as set forth in claim 101, wherein the musical perception parameters includes a set of musical variables, changes in the musical variables, and relationships between the variables.

104. A method, as set forth in claim 101, wherein the step of generating a graphic display includes the step of generating at least one of a wave, sonographic, or spectrographic graphs of the first and second acoustic signals.

105. A method, as set forth in claim 101, wherein the step of generating a graphic display includes the step of generating a display representing the first and second musical data signals in musical notation.

106. A method, as set forth in claim 103, wherein the musical variables include melody and rhythm.

107. A method for analyzing a system using musical perception sound analysis, including the steps of:
   recording an acoustic event of the system and responsively generating an acoustic event signal; and,
   receiving the acoustic event signal and responsively monitoring the system as a function of a set of musical perception parameters and responsively identifying a presence of a predetermined condition of the system, the predetermined condition being defined by the musical perception parameters.

108. A method, as set forth in claim 107, including the step of analyzing the acoustic events against a developed syntax defined in terms of rhythm and melody, wherein rhythm includes patterns of attack, decay, and cessation, and melody includes patterns of pitch and timbre.

109. A method, as set forth in claim 107, including the step of recording an actual acoustic event of the system and responsively generating an actual acoustic event signal and wherein the step of monitoring the system includes the steps of:
   receiving the actual acoustic event signal; and,
   analyzing the actual acoustic event signal using the set of musical perception parameters.

110. A method, as set forth in claim 107, wherein the set of musical perception parameters includes a set of musical variables, changes in the musical variables, and relationships between the variables.

111. A method, as set forth in claim 110, wherein the musical variables includes melody and rhythm.

* * * * *

UNITED STATES PATENT AND TRADEMARK OFFICE
CERTIFICATE OF CORRECTION

PATENT NO. : 6,719,707 B1
DATED : April 13, 2004
INVENTOR(S) : Montgomery et al.

It is certified that error appears in the above-identified patent and that said Letters Patent is hereby corrected as shown below:

Column 9,
Line 46, after "29." delete "herein" and insert -- wherein --.
Line 54, after rhythm delete "an d" and insert -- and --.
Line 59, after "25," delete "herein" insert -- wherein --.

Column 13,
Line 51, after "variables;" move rest of text to next line (line 52); this text should be a separate indented paragraph.

Signed and Sealed this

Twenty-seventh Day of July, 2004

JON W. DUDAS
*Acting Director of the United States Patent and Trademark Office*